United States Patent [19]

Newman et al.

[11] Patent Number: 4,845,042

[45] Date of Patent: Jul. 4, 1989

[54] ADJUVANT FOR IMMUNIZATION

[75] Inventors: John F. E. Newman; Donald A. Hendry, both of Grahamstown, South Africa

[73] Assignee: South African Inventions Development Corporation, Pretoria, South Africa

[21] Appl. No.: 719,851

[22] Filed: Apr. 4, 1985

[30] Foreign Application Priority Data

Apr. 13, 1984 [ZA] South Africa ............... 84/2763

[51] Int. Cl.$^4$ ............... G01N 33/532; A61K 39/39; A61K 39/02; A61K 39/12; A61K 39/385

[52] U.S. Cl. ............... 436/545; 435/5; 435/7; 424/86; 424/88; 424/89; 424/92; 424/85.8; 424/87; 424/485; 514/773; 514/776; 514/964; 514/965; 436/543; 436/547; 436/808; 427/3

[58] Field of Search ............... 514/773, 776, 964, 965; 424/22, 36, 86, 88, 89, 85, 87, 91, 92; 530/812, 817; 436/545, 543, 547, 808; 435/5, 7; 427/3

[56] References Cited

U.S. PATENT DOCUMENTS

| | | | |
|---|---|---|---|
| 3,937,668 | 2/1976 | Zolle | 424/36 X |
| 4,107,288 | 8/1978 | Oppenheim et al. | 424/36 X |
| 4,147,767 | 4/1979 | Yapel, Jr. | 424/36 X |
| 4,269,821 | 5/1981 | Kreuter et al. | 424/22 X |
| 4,357,259 | 11/1982 | Senyei et al. | 514/776 X |
| 4,367,222 | 1/1983 | Kasper | 424/85 X |
| 4,423,034 | 12/1983 | Nakagawa et al. | 424/85 |
| 4,438,208 | 3/1984 | Deftos | 436/545 X |
| 4,585,740 | 4/1986 | Vander Laan | 436/545 X |

FOREIGN PATENT DOCUMENTS

| | | |
|---|---|---|
| 2002387 | 2/1979 | United Kingdom . |
| 1545332 | 5/1979 | United Kingdom . |
| 2041517 | 9/1980 | United Kingdom . |
| 2062644 | 5/1981 | United Kingdom . |
| 2066203 | 7/1981 | United Kingdom . |
| 1597561 | 9/1981 | United Kingdom . |
| 2079289 | 1/1982 | United Kingdom . |
| 2101630 | 1/1983 | United Kingdom . |
| 2160312 | 12/1985 | United Kingdom . |

OTHER PUBLICATIONS

Remy et al., The Lancet, vol. 2: 68–70 (1978).
Lee et al., Science, vol. 213: 233–235 (1981).

*Primary Examiner*—Esther M. Kepplinger
*Attorney, Agent, or Firm*—Millen & White

[57] ABSTRACT

The invention provides an immunizing agent or preparation e.g. a vaccine for parenteral administration comprising particles of coalesced and covalently interlinked physiologically compatible proteinaceous molecules and, entrapped in these particles, an immunogen adapted to be released by the gradual proteolysis of the particles and, when so released, being of sufficient size to elicit an immuno response to characteristic immunogenic determinants of the immunogen. The proteinaceous molecules are preferably homotypic for the animal to be immunized. Preferably, the particles or molecules carrying the immunogenic determinants are cross-linked to the proteinaceous molecules.

37 Claims, 1 Drawing Sheet

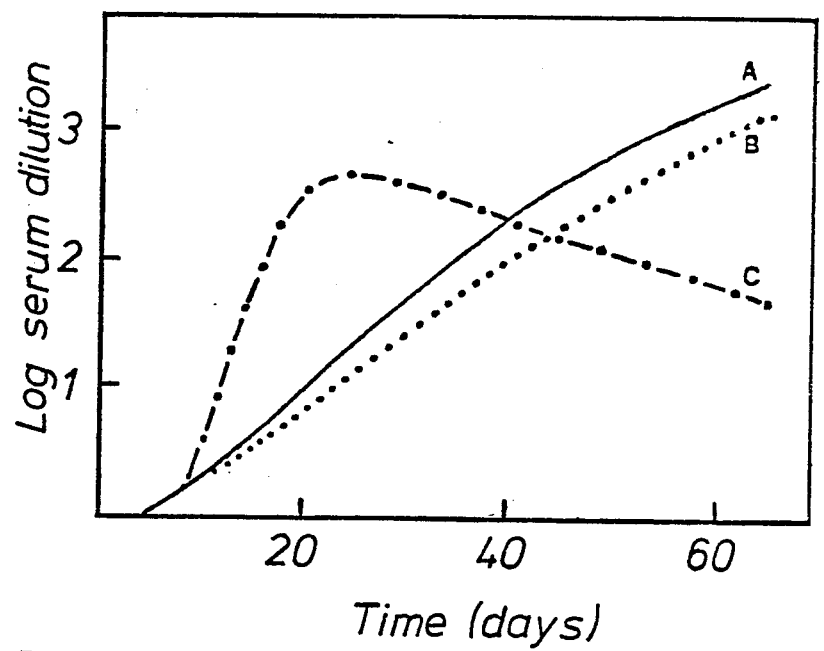

ADJUVANT FOR IMMUNIZATION

FIELD OF THE INVENTION

The present invention relates to an immunizing agent or preparation, more particularly injectable and preferably for use as a vaccine, comprising features which in combination provide an adjuvant effect, including a prolonged immunogenic stimulus.

BACKGROUND OF THE INVENTION

In recent years great advances and important new discoveries have been made in immunology in general and in the development of new or more potent vaccines in particular. A better understanding of some of the underlying principles is beginning to emerge in the art, but many phenomena and mechanisms related thereto are still not understood or are understood incompletely only. Some aspects of the state of the art relating to adjuvants are well summarized in a recent article by Audibert and Chedid, entitled "Recent Advances Concerning the Use of Muramyl Dipeptide Derivatives as Vaccine Potentiators" in "New Developments with Human and Veterinary Vaccines" (1980) Allen R. Liss, Inc., 150 fifth avenue, N.Y.1001, page 325-338, wherein it is stated: "There exists a general consensus for the requirements of adjuvants in the following cases: (a) prolonging the efficacy of immunization; (b) avoiding the need for repeated injections; (c) decreasing the dose of antigen to reduce side effects and/or its costs; (d) increasing the immunogenicity or (e) augmenting the immunological responsiveness of certain hosts; (f) obtaining more selective responses." In the conclusions these same authors state: "It can be assumed reasonably that many new vaccines will contain two kinds of well-defined components, a specific antigenic stimulus and a non-specific adjuvant. Until very recently immuno potentiating engines [sic] were complex and ill-defined."

The classical example of a highly effective adjuvant for eliciting a strong and persistent immuno response to an injected immunogen (which is inter alia also discussed in the above article) is Freund's complete adjuvant, a combination of a mineral oil emulsion and mycobacteria. Also well-known in Freund's incomplete adjuvant which differs from the complete adjuvant in that it lacks the mycobacteria component. Both adjuvants are used extensively in veterinary medicine and for the immunization of laboratory animals in order to produce antibody preparations for use, e.g. as antisera or immuno reagents (such as diagnostics). However, neither of these adjuvants is acceptable for clinical purposes in humans, because of the presence of mineral oil and in the case of Freund's complete adjuvant also because of side effects resulting from the mycobacteria, in particular necrosis at the injection site. These factors naturally also are to be considered disadvantageous when treating animals. Other adjuvants which achieve a prolonged immunogenic response are protein adsorbents such as aluminum hydroxide or aluminium phosphate, used for example in influenza vaccines. However, these substances which achieve a slow release effect have the disadvantage of being foreign to the body. They do not contribute to the immunogenicity of the immunigen itself, once the immunogen is released from adsorption.

It is known to improve the immunogenicity of immunogens or to impart immunogenicity to haptens which on their own are immunogenically inactive, by covalently aggregating these haptens or immunogens or linking them covalently to carrier molecules or particles such as proteins in order to produce immunogenic particles of increased size and having specificity for the hapten or immunogen. For example, H. Gharib et al (J.Clin. Endocrinol. and Metabolism (1971) 33, 509-516) describe the covalent linking of $T_3$ to serum albumin derived from various animal species (human, bovine, rabbit) and using the resulting conjugates to elicit antibodies against $T_3$ in rabbits for use in radio-immuno assays (RIA). These conjugates, however, have a short half-like, being soon destroyed in the body of the animal. Accordingly, frequent repetitions of the immunizing injections (weekly) are necessary until the required antibody level is attained and booster injections are necessary thereafter.

In the aforegoing context it is also known to covalently link haptens or immunogens by a variety of difunctional linking agents to bacterial cells or particles, preferably stripped of their natural immunogenic determinants ("naked bacteria") to produce improved immunogens. The substantial improvements in immunogenicity thus attained is believed to be due to the increased particle sizes as well as an adjuvant effect of the bacterial components(s) (UK published patent application No. GB 2,101,630 A in the name of the present applicant).

Others, e.g. the aforesaid authors Audibert and Chedid propose as an alternative new generation of adjuvants certain muramyl dipeptide derivatives (MDP - cf Audibert et al,loc.cit.). MDP represents part of the bacterial glycopeptide. Even these new adjuvants represent substances foreign to the host body, and pyrogenicity has been observed. Certain derivatives are also immunogenic on their own, i.e. have the property of sensitizing to MDP. Some toxicological criteria pertaining to the use of these adjuvants, e.g. auto-immune or allergic reactions following the administration of vaccines comprising MDP are still unknown.

Accordingly it is clear that there still exists a long felt need for adjuvants which overcome or mitigate all or at least some of the aforesaid disadvantages and/or which offer novel advantages.

THE INVENTION

According to one aspect of the present invention there is now provided an immunizing agent or preparation as set out in the opening paragraph, comprising particles of coalesced and covalently interlinked physiologically compatible proteinaceous molecules and, entrapped in these particles, an immunogen adapted to be released by the gradual proteolysis of the particles and, when so released, being of sufficient size to elicit an immuno response to characteristic immunogenic determinants of the immunogen.

Particularly where the agent or preparation is to be administered parenterally, it is important that the proteinaceous molecules of the particles are so chosen that they themselves will not elicit an adverse immuno response. Therefore, according to an important preferred feature of the invention, the proteinaceous molecules are homotypic for the animal to be immunized. This is in contrast to prior art teachings (R. G. White "Immunogenicity. Frontiers of Biology"; volume 25 (1971), Amsterdam, pages 112-129, on page 115) according to which a stronger antibody response will develop when using protein carriers from an animal species other than that injected. In contrast to such teaching, by using homotypic proteinaceous substance, adverse immuno reactions, e.g. effects such as hypersensitivities, allergies or even anaphylactic shock may be mitigated against. It is also improbable in that case that the particles are attacked by antibodies and become encapsuled by the antibodies or by a surrounding zone of antigen-antibody precipitate, whereby the required release of immunogen is subsequently blocked (R. G. White; loc.cit. at page 122).

The term "proteinaceous substances" is intended to include true (complete) proteins as well as compatible proteins derivatives and covalently interlinkable fragments of proteins, e.g. polypeptides. However, normal proteins are preferred and in particular albumin, more particularly serum albumin. Such serum albumin should preferably, in order to be homotypic, be derived from the same species of animal (including humans) as that animal which is to be immunized with the agent or preparation. Human serum albumin when used in the manufacture of human vaccines offers the economic advantage of being readily available, e.g. from the commercial fractionation of dated blood supplies. Merits are also considered to reside in the use of synthetic peptides for use in vaccines, e.g. having immunogen or haptens covalently bonded to the peptide chain.

The particles of coalesced and covalently interlinked proteinaceous molecules have to be dimensioned in a manner best compatible with the intended use. For parenteral administration, and in particular for intramuscular or subcutaneous administration (of which the former is at present preferred) the particles preferably do not exceed 500 μm in diameter, whilst the minimum size is determined by the minimum number of molecules needed to entrap the immunogen effectively. If the particles are too large, immunization will be difficult. If they are too small, the ratio of surface area to volume will be too great and the rate of release and disappearance of the immunogen will be too high. The preferred particle size is in most cases within the range of 50 to 300, more preferably 100 to 200 μm.

Preferably the particles are of substantial spherical configuration.

Such particles, incorporating the immunogen may be prepared by a process according to the invention which comprises polycondensing polymerizing by covalent reaction) the proteinaceous molecules in a solution thereof containing also dissolved or suspended an immunogen or hapten, using a difunctional linking agent of other polycondensating agent for the proteinaceous molecules, if required in the presence of an emulsifying agent, and dispersing the resulting suspension with controlled and prolonged agitation in an oil solution to produce an emulsion, followed by coalescence of the polycondensed proteinaceous molecules into beads, and in the case of a hapten being employed, linking such hapten during or prior to the aforesaid process steps sufficiently strongly, preferably covalently, to a carrier suitable to transform the hapten into an immunogen.

The step of emulsifying and coalescing in the oil solution is preferably carried out in a vortex mixer. The rate of stirring should be controlled carefully to a value determined empirically to produce the desired size of the beads (under the prevailing process conditions such as shape and dimensions of the stirrer and vessel, viscosity, mode of injection into the oil solution).

A suitable oil is a vegetable oil such as sunflower or maize (corn) oil, the former being preferred. The solvent for the oil is normally a non-polar solvent. e.g. ether or petroleum ether, the latter being preferred.

The above process is analogous to a procedure described by T K Lee et alia (Science, 213, 233-235). However, in that method the beads were formed so as to entrap a variety of drugs in slow release form, in particular the drug progesterone. Progesterone is immunologically inactive. In the method of Lee et alia progesterone is not converted into an immunogen, and such immunogen formation would indeed be incompatible with the object of that procedure. The purpose of slow release administration would be defeated by the formation of antibodies against the drug. In the case of the described example of progesterone, such induced immunity would be particularly serious, because progesterone is also a substance occurring naturally in the body. Indeed, it is stressed by Lee et al that "rabbits that had received injections for several months did not show any adverse immunological symptoms".

As in the case of the method according to Lee et al, glutaraldehyde may be used as the polycondensation agent. However, many other difunctional linking agents are known in the art which can be employed for the purposes of the present invention in a similar manner to glutaraldehyde. In this respect reference is made to the large number of linking agents and methods of use thereof described in the aforementioned UK patent application No. GB 2,101,630 A that same disclosure relating to the use of linking agents is also contained in U.S. Pat. No. 4,550,019, in particular in column 7, line 61 to column 9, line 15 and in numerous examples thereof. From that disclosure the manner in which these linking agents may be applied for purposes of the present invention will be readily apparent to those skilled in the art. Accordingly that disclosure is to be read as if it were part of the present specification.

If the substance carrying the desired immunogenic determinants to be used in accordance with the invention is a hapten, such hapten must be linked to a carrier, preferably covalently, to convert the hapten into an immunogen. Such carrier may in fact be provided by the proteinaceous molecules used for forming the particles on condition that the haptens are linked sufficiently strongly to those molecules. such linkage may be brought about either before or during the proteinaceous molecules being subjected to the polycondensation and/or coalescing. Such linkage may be brought about using the same difunctional linking agents as referred to above in the context of the polycondensation, the choice of linking agent being of course subject to the nature of available chemical groups on the hapten suitable for a linking reaction. In fact, in some preferred embodiments of the invention the linkage of the haptens takes place simultaneously with and using the same linking agent as used for the polycondensation.

What has been described above, in preferred not only in the case of haptens, but also in the case of substances which are already immunogens, even relatively strong immunogens such as virus or bacterial particles or ricketsia or bacterial toxins being used in accordance with the invention. The already existing immunogenicity of such substances can be further enhanced in that manner.

Haptens or immunogens used in practicing the invention may, however, also be linked covalently to carriers other than the proteinaceous molecules (e.g. albumin) used for the polycondensed particles, e.g. where such carriers have active groups particularly suitable for limking to the hapten or immunogen and/or where the carrier has properties which enhance the desired immunigenicity. Such carriers may themselves be proteins or proteinaceous compounds (preferably of high modecular weight). The carriers may also be bacterial fragments or particles or cells, e.g. "naked bacteria" as described in UK patent application No. GB 2,101,630 A.

The degree of polycondensation of the proteinaceous molecules is a factor which affects the rate at which the particles will undergo proteolysis in the body to release the entrapped immunogen and thereby the rate of release of immunogen. This is therefore a variable which can be used to adjust e.g. by simple trial and error the rate of release of immunogen to a desired optimum. A preferred parameter for adjusting this variable is the concentration of polycondensation or linking agent employed in the polycondensation. For example, in the case of serum albumin, polycondensed with glutaraldehyde, its concentration for most of the purposes herein contemplated is found to be in the region of 0.3 to 1.8%, preferably 0.5 to 1.5%, say 1%. If the concentration of linking agent is too high, the biodegradabilty of the particles becomes too low.

The range of practical mass ratios of hapten or immunogen to proteinaceous particle material is very large and depends inter alia on the concentration of exposed effective immunogenic determinants on the hapten or immunogen in relation to its mass. In the case of purified virus serving as the immunogen, a mass ratio of virus to serum albumin in the range of from 1:10 000 to 1:100 can yield useful results, a range of from 1:5000 to 1:500 being more preferred, for example 1:2000. These data which apply to virus are also indicative of the concentrations required for other immunogens or haptens.

For immunological studies, e.g. involving the observation of the rate of release of the immunogen, the latter may may radioactively labeled in a manner known per se.

The invention is considered to have particular merit in the context of the protective immunization of animals, (including humans) against disease caused by pathogenic organisms, in particular viruses, ricetsia and bacteria. Accordingly, the preferred haptens or immunogens used in the agent of process according to the invention are those which carry the immunogenic determinants which are characteristic for such organisms or at least a portion thereof or of toxins adequate to elicit an effective immuno response against such organisms or toxins.

Individual beads, e.g. of a polyvalent vaccine, may each incorporate a plurality of antigens, immunogens or haptens, the latter covalently bonded to a carrier (which may be the proteinaceous molecule integer of the beads). A polyvalent vaccine may also be made up of a mixture of beads which differ from one another in respect of the identity of antigens, immunogens or haptens incorporated therein.

Is is an advantage of the invention that the agent or preparation, e.g. for use as a vaccine, can be stored in a dry form.

The scope of the invention also extends to a process for the active immunizing of animals against immunogenic determinants which comprises the administration, more particularly the parenteral administration of an agent or preparation according to the invention described above in a dosage designed to produce an effective immuno response. Suitable dosages will, of course, differ from case to case and should be optimized empirically for a given vaccine. Parenteral administration in this context may more particularly be by the intermuscular or subcutaneous route, preferably the former. Generally it will be found that the beads according to the invention are too large for intravenous use.

The order of magnitude of the dosage can be estimated from dosage rates applicable to conventional comparable vaccines and the estimated rate of release of the immunogen. In the case of virus particles serving as the immunogen typical dosage rates would be in the range of 1 to 100 µg of virus per kg of host, preferably from 3 to 30 µg/kg, e.g. 10 µg per/kg.

Particular effects may be attained by the combined administration of immunogen in unentrapped form and immunogen entrapped in particles as described above. the unentrapped immunogen is administered alone will initially elicit a relatively more rapid, but less persistent immuno response, apparently yielding predominantly IgG antibodies of the $\gamma_1$ type whilst the entrapped immunogen will initially elicit a much slower response which, however, persists over a considerably longer period and may eventually taper off to a persistent antibody level, mainly of $\gamma_2$ antibodies, which are particularly desirable. The combined application of immunogen in the two forms - e.g. supplied as a kit or combined in one vaccine - will result in a combination of these two effects, i.e. a rapid response combined with a persistent high antibody titer, moreover there may result synergistic effects.

The processes may be applied to the active protective immunization of the animals against disease or to the eliciting of antibodies for recovery in the form of antibody preparations, e.g. for use an antisera, anti-toxins, anti-venoms and the like, i.e. for the passive immunization of humans or animals against pathological conditions such as infective disease or poisoning. Such antibody preparations may, however, also be supplied for use as immuno reagents, e.g. in pathology, diagnostics, pharmacoketics, forensic and other laboratory applications.

A particular use for antibody preparations which can be manufactured with the aid of the present invention is in immuno assays, e.g. RIA or ELISA. With regard to these methods, the techniques described in Gharib et al. (loc.cit.) and UK patent application No. GB 2,101,630 A may be applied mutatis mutandi.

The antibodies may be supplied as immuno assay kits, e.g. (in the case of RIA) comprising as separate items the specific antibody preparation in a standardised solution, e.g., in serum solution, a standard solution for dilution, e.g. serum dissolved in buffer, a standard for the substance to the tested for and the same substance radioactively labeled.

BRIEF DESCRIPTION OF THE DRAWINGS

The accompanying drawing shows three curves of IgG levels in serum of rabbits, immunized with a single injection of virus: Curve A, Virus in Freund's adjuvant; Curve B, virus polymerized into rabbit serum albumin beads; Curve C, virus alone. The ELISA antibody titer is expressed as the log serum dilution giving an absorbence reading at 450 nm which was 0.25 units above control levels.

EXAMPLES

Example 1

100 μg of purified virus was added to 200 mg of rabbit serum albumin in 1 ml of phosphate buffered saline at pH 7.6 containing 0.1% sodium dodecyl sulphate. Polycondensation was then iniated by the addition of gutaraldehyde to final concentration of 1%. The suspension was immediately dispersed using a vortex mixer and after 10 seconds was rapidly added to 100 ml of a mixture of sunflower oil and petroleum ether (1:4 by volume) using a 2 ml syringe fitted with an 18 gauge needle. The resulting emulsion was stirred at a constant rate of stirring of 1500 rpm (2.5 cm stirrer bar, vessel diameter 7.5 cm) for one hour at room temperature to allow full polycondensation and uniform bead formation to occur. The rate of stirring was carefully controlled with a stroboscope, because the rate of stirring affects the size of the beads produced. To some extent the technique of injecting the polycondensating protein into the oil solution as well as the diameter of the vessel used will influence the size of the beads. However, these are factors which can readily be adapted by the ordinary skilled operator by trial and error. Also, it is found that other vegetable oils, e.g. maize can be used instead of sunflower oil. However, sunflower oil was found to result in more uniform bead sizes. In the present example experimental conditions were adjusted to cause beads of 100 and 200μ in diameter to be formed which are particularly suitable for injection into experimental animals. The beads were collected by allowing them to settle out of the oil mixture and were washed three times with petroleum ether and then dried for 20 minutes using a freeze drying apparatus.

By using radioactively labeled virus, it was possible to demonstrate that more than 90% of the virus in the mixture became complexed into beads using the procedure described and could not be removed by repeated washing with petroleum ether. The beads were observed under the scanning electronmicrograph. They are of relatively smooth and regular spherical configuration with only minor protrusions. The above procedure was carried out with rabbit serum albumin because the beads were intended to be injected subsequently into rabbits. Precisely the same procedure can be followed with serum albumin of other species intended for injection into corresponding species of animals or humans.

Also for experimental purposes Nodamura virus, a nonpathogenic pathogenic small RNA virus was used. However, the procedure is applicable to any kind of virus and can readily be applied also to other immunogens or haptens having linking groups capable of reacting with glutaraldehyde as have virus particles. In the present case the experimental conditions were such that the virus particles would not only become physically entrapped in the beads, but would also undergo covalent linkage to the protein of the beads.

Example 2

Comparative immunization test

The beads containing entrapped virus were compared with other preparations for eliciting an immune response. Three experiments were undertaken. Each experiment was conducted with a group of five adult rabbits inocculated intramuscularly with an identical dosage (A) Virus emulsified in Freund's complete adjuvant (B) Virus entrapped in protein beads (according to Example 1); (C) Virus in phosphate buffered saline.

At three to four day intervals each rabbit was bled from the ear and the separated serum stored at −20°. Serum antibody (IgG) levels (ampoules of sera from each bleeding) were determined using the enzyme-linked immunosorbent assay (ELISA). The ELISA results are reflected in the accompanying drawing and show that each Nodamura virus preparation when inocculated into rabbits was a potent immunogen and that maximum virus specific antibody (IgG) titers occur at different times. Rabbits immunised with rabbit serum albumin beads contaiing the entrapped virus and those with virus in Freund's adjuvant yielded antibody titers which were still increasing 60 days after inoculation, as illustrated in the drawing. In the case of the rabbits immunized with the albumin beads according to the invention further experiments revealed that the antibody titers would continue to rise for a total of about 110 days and then reach a plateau which was found to persist even after 150 days. Rabbits immunized with virus alone exhibit a more rapid initial rise in antibody titer reaching a maximum at a about 20 days after the inoculation followed by a gradual decline. The maximum was less than the eventual titers attained in the remaining two experiments. In fact it was more than one log factor below the plateau level eventually attained with the albumin beads according to the invention. No significant fluctuations of body temperature or weight were observed in any of the rabbits during the 60 day period of the experiment. However, rabbits immunized with virus in Freund's complete adjuvant and killed 10 days later revealed significant necrosis and oil at the injection site. Rabbits immunized with the albumin polycondensateentrapped virus had residual beads at the injection site after 10 days, but, in common with animals inoculated with virus alone showed no signs of inflammation or necrosis.

To test the specificity of the humoral antibodies produced in the vaccinated rabbits, a 30 day serum sample from each animal group was mixed with Nodamura virus prior to inoculation into susceptible suckling mice. With each test serum sample complete neutralization of virus infectivity occured.

The test also demonstrates some of the advantages to be attainable from a combined vaccine comprising virus entrapped in albumin beads and free virus, namely a more rapid initial response followed by a continuing rise in titer to an eventual higher plateau.

The experiments also revealed that the dosage rate chosen in this experiment could in practice both be lowered or increased substantially.

The beneficial results according to the invention as herein described are particularly surprising and unexpected when considered in the light of M.H. Remy and M. J. Poznansky, The Lancet, July 8, 1978, pp. 68–70. These authors found that when immunogenic substances, namely enzymes are crosslinked (with glutaraldehyde) to polymers of albumin, these substances lose their immunogenicity completely, even though their enzymatic effect in enzyme replacement therapy is preserved and even enhanced.

Example 3

A vaccine was prepared in substantially the manner described in Example 1 against Clostridium botulinum toxin D using 2.25 parts by mass of toxin D and 400 parts by mass of rabbit serum albumin. The esulting beads were suspended in phosphate buffer saline as in Example 2. Each rabbit was vaccinated subcutaneously once only with 225 micrograms of toxin D in 40 mg rabbit serum albumin. The rabbits were bled after 6 weeks and 12 weeks respectively, and the serum was separated and tested for its suitability as an antiserum as follows:

Mice were injected with lethal dosages of toxin D mixed with the antiserum. All mice survived.

The aforegoing description will enable those skilled in the art to practice the invention within the full scope of the claims with a variety of immunogens, and a variety of proteinaceous molecules, If necessary with such relatively minor modifications of procedure as will occur to the skilled person supplemented where necessary by simple exploratory experiments, e.g. directed to the optimum parameters for attaining maximum immunogenicity.

We claim:

1. An immunizing agent or preparation comprising particles of coalesced and covalently interlinked physiologically compatible proteinaceous momlecules and, entrapped in these particles, an immunogen adapted to be released by the gradual proteolysis of the particles and, when so released, being of sufficient size to elicit an immune response to characteristic immunogenic determinants of the immunogenic.

2. A pharmaceutical composition in parenteral form comprising an agent or preparation as claimed in claim 1 and an acceptable carrier for parenteral administration.

3. Agent or preparation as claimed in claim 1, wherein the proteinaceous molecules of the particles are so chosen that they themselves will not elicit an immune response.

4. Agent or preparation as claimed in claim 3, wherein the proteinaceous molecules are homotypic for the animal to be immunized.

5. Agent or preparation as claimed in claim 1, wherein the proteinaceous substance is albumin.

6. Agent or preparation as claimed in claim 5 wherein the albumin is serum albumin.

7. Agent or preparation as claimed in claim 5 wherein the albumin is derived from the same species of animal which is to be immunised with the agent or preparation.

8. An agent or preparation according to claim 7, wherein said animal is human.

9. Agent or preparation as claimed in claim 1 intended for parenteral administration, having a particle size not exceeding 500 μm.

10. Agent or preparation as claimed in claim 9, having a particle size of 50 to 300 μm.

11. Agent or preparation as claimed in claim, wherein the particles are of substantially spherical configuration.

12. Agent or preparation as claimed in claim 1 wherein the particles have been prepared by a process which comprises:
    adding to one another, in a liquid medium, to form a joint solution or suspension, proteinaceous molecules and an immunogen or hapten;
    polycondensing the proteinaceous molecules by adding to the solution or suspension an effective amount of a difunctional linking agent or a polycondensing agent for the proteinaceous molecules, optionally in the presence of an emulsifying agent;
    dispersing the resulting suspension with controlled and prolonged agitation in an oil solution to produce an emulsion; and
    coalescing the polycondensed proteinaceous molecules into beads;
    and in the case of a hapten being employed, linking such hapten during or prior to the aforesaid process steps sufficiently strongly to a carrier suitable to transform the hapten into an immunogen.

13. Agent or preparation as claimed in claim 1, wherein the immunogen comprises a substance having immunogenic determinants, which is covalently bonded to the proteinaceous molecules.

14. Agent or preparation as claimed in claim 1, wherein the immunogen comprises a substance having the desired immunogenic determinants, covalently bonded to a carrier other than the proteinaceous molecules.

15. Agent or preparation as claimed in claim 14, wherein the carrier is a bacterial fragment, particle or cell.

16. Agent or preparation as claimed in claim 1, wherein the mass ratio of immunogenic substance to proteinaceous molecules is 1:10 000 to 1:100.

17. Agent or preparation as claimed in claim 16, wherein the ratio is 1:5000 to 1:500.

18. Agent or preparation as claimed in claim 16, whrein the immunogen is purified virus.

19. Agent or preparation as claimed in clailm 1, wherein the immunogen is radioactively labelled.

20. Agent or preparation as claimed in claim 1 wherein the immunogen comprises a toxin.

21. Agent or preparation as claimed in claim 20 wherein the immunogen comprises a bacterial toxin.

22. Agent or preparation as claimed in claim 1 wherein the immunogen is represented by a plurality of different antigens, immunogens or haptens, the latter covalently bonded to a carrier, adapted as a polyvalent vaccine.

23. Agent or preparation as claimed in claim 22 of which each individual particle incorporates the plurality of antigens, immunogens or haptens.

24. An agent or preparation as claimed in claim 1 stored in a dry form.

25. Agent or preparation as claimed in claim 1, wherein the immunogen is a pathogenic microorganism or part thereof having immunogenic determinants of that microorganism.

26. An immunizing agent or preparation according to claim 1, further containing in a free, untrapped form, an immunogen carrying said immunogenic determinants.

27. A pharmaceutical composition in parenteral form comprising an agent or preparation as claimed in claim 26 and an acceptable carrier for parenteral administration.

28. A process of actively immunizing an animal against at least one pathogenic organism, comprising administering parenterally to said animal an amount of an agent or preparation according to claim 1 to protect said animal against said at least one pathogenic organism.

29. A method according to claim 28, wherein said administering is conducted by the intramuscular or subcutaneous route.

30. A process for producing antibody preparations which comprises actively immunizing an animal by parenterally administering an immunizing agent or preparation comprising particles of coalesced and covalently interlinked physiologically compatible proteinaceous molecules and, entrapped in these particles, an immunogen adapted to be released by the gradual proteolysis of the particles and, when so released, being of sufficient size to elicit an immune response to characteristic immunogenic determinants of the immunogen and recovering from the animal antibodies elicited by such immunization.

31. Process as claimed in claim 30, comprising the further step of incorporating the antibody preparations in an immuno assay kit.

32. A process for the manufacture of an immunizing agent or preparation comprising particles of coalesced and covalently interlinked physiologically compatible proteinaceous molecules and, entrapped in these particles, an immunogen adapted to be released by the gradual proteolysis of the particles and, when so released, being of sufficient size to elicit an immune response to characteristic immunogenic determinants of the immunogen which process comprises:

adding to one another, in a liquid medium, to form a joint solution or suspension, proteinaceous molecules and an immunogen or hapten, initiating polycondensation of the proteinaceous molecules by adding to the solution or suspension an effective amount of a difunctional linking agent or a polycondensation agent, optionally in the presence of an emulsifying agent, dispersing the resultant suspension with the aid of the agitation in an oil solution to produce an emulsion of the oil and the suspension, including the proteinaceous molecules subjected to polycondensation and the immunogen or hapten, and coalescing the proteinaceous molecules into beads containing the immunogen or hapten entrapped in a matrix of the proteinaceous molecules which are polycondensed.

33. A process as claimed in claim 32, wherein a hapten is employed and wherein the hapten is linked to a carrier and is thereby transformed into an immunogen.

34. A process as claimed in claim 32, wherein the hapten is linked to the proteinaceous molecules as a carrier.

35. A process as claimed in claim 32, wherein the immunogen or hapten is bonded covalently to the proteinaceous molecules.

36. A kit comprising:
   (a) in a first container, an immunizing agent or preparation comprising particles of coalesced and covalently interlinked physiologically compatible proteinaceous molecules and, entrapped in these particles, an immunogen adapted to be released by the gradual proteolysis of the particles and, when so released, being of sufficient size to elicit an immune response to characteristic immunogen determinants of the immunogen, and
   (b) in a second container, in a free, untrapped form, an immunogen carrying said immunogenic determinants.

37. A method of eliciting antibodies in an animal comprising actively immunizing the animal or human with an immediately available immunogen carrying immunogenic determinants against which an immune response is to be elicited and in addition with an immunization agent or preparation comprising particles of coalesced and covalently interlinked physiologically compatible proteinaceous molecules and, entrapped in these particles, an immunogen carrying the immunogenic determinants, adapted to be released by the gradual proteolysis of the particles and, when so released, being of sufficient size to elicit an immune response to the immunogenic determinants.

* * * * *

UNITED STATES PATENT AND TRADEMARK OFFICE
CERTIFICATE OF CORRECTION

PATENT NO. : 4,845,042

DATED : July 4, 1989

INVENTOR(S) : JOHN F.E. NEWMAN ET AL

It is certified that error appears in the above-identified patent and that said Letters Patent is hereby corrected as shown below:

Column 9, claim 1, line 22:

reads "ologically compatible proteinaceous momlecules and,"

should read -- ologically compatible proteinaceous molecules and, --

Column 9, claim 1, line 27:

reads "minants of the immunogenic."

should read -- minants of the immunogen. --

Column 9, claim 11, line 53:

reads "agent or preparation as claimed in claim, wherein"

should read -- agent or preparation as claimed in claim 1, wherein --

UNITED STATES PATENT AND TRADEMARK OFFICE
CERTIFICATE OF CORRECTION

PATENT NO. : 4,845,042
DATED     : July 4, 1989
INVENTOR(S) : JOHN F.E. NEWMAN ET AL It is certified that error appears in the above-identified patent and that said Letters Patent is hereby corrected as shown below:

Column 10, claim 19, line 26:
    reads "agent or preparation as claimed in clailm 1,"
should read -- agent or preparation as claimed in claim 1,--

Column 12, claim 36, line 18:
    reads "response to characteristic immunogen determi-"
Should read -- response to characteristic immunogenic
          determi- --

Signed and Sealed this

Twenty-fourth Day of April, 1990

*Attest:*

HARRY F. MANBECK, JR.

*Attesting Officer*     *Commissioner of Patents and Trademarks*